(12) United States Patent
Taber et al.

(10) Patent No.: US 9,561,060 B2
(45) Date of Patent: Feb. 7, 2017

(54) INTERSPINOUS IMPLANTS WITH ADJUSTABLE HEIGHT SPACER

(71) Applicant: Zimmer Biomet Spine, Inc., Broomfield, CO (US)

(72) Inventors: Justin Taber, Lafayette, CO (US); Patrick Hunt, Denver, CO (US); Andrew Lamborne, Golden, CO (US); Randall G. Mast, Denver, CO (US); William Sandul, Broomfield, CO (US)

(73) Assignee: Zimmer Biomet Spine, Inc., Broomfield, CO (US)

( * ) Notice: Subject to any disclaimer, the term of this patent is extended or adjusted under 35 U.S.C. 154(b) by 0 days.

(21) Appl. No.: 14/650,418

(22) PCT Filed: Dec. 31, 2013

(86) PCT No.: PCT/US2013/078474
§ 371 (c)(1),
(2) Date: Jun. 8, 2015

(87) PCT Pub. No.: WO2014/106243
PCT Pub. Date: Jul. 3, 2014

(65) Prior Publication Data
US 2015/0313650 A1    Nov. 5, 2015

Related U.S. Application Data

(60) Provisional application No. 61/747,748, filed on Dec. 31, 2012.

(51) Int. Cl.
*A61B 17/70* (2006.01)

(52) U.S. Cl.
CPC ....... *A61B 17/7068* (2013.01); *A61B 17/7067* (2013.01)

(58) Field of Classification Search
CPC .................. A61B 17/7067; A61B 17/7068
See application file for complete search history.

(56) References Cited

U.S. PATENT DOCUMENTS

| 6,695,842 B2 * | 2/2004 | Zucherman | A61K 31/37 606/249 |
| 7,727,233 B2 * | 6/2010 | Blackwell | A61B 17/7068 606/251 |

(Continued)

FOREIGN PATENT DOCUMENTS

| WO | WO-2009101539 A2 | 8/2009 |
| WO | WO-2011/094062 | 8/2011 |
| WO | WO-2011141869 A1 | 11/2011 |

OTHER PUBLICATIONS

International Search Report and Written Opinion of the ISA for PCT/US2013/078474, ISA/KR, Daejeon, mailed Apr. 3, 2014.

(Continued)

*Primary Examiner* — Ellen C Hammond
*Assistant Examiner* — Stuart S Bray
(74) *Attorney, Agent, or Firm* — Schwegman Lundberg & Woessner, P.A.

(57) ABSTRACT

The present invention provides spinous process implants and associated methods. In one aspect of the invention, the implant includes at least one extension with a superior lobe pivotally connected to an inferior lobe, such as by a hinge, to allow unfolding of the at least one extension from a folded position to an unfolded position. In certain aspects, the folding extension may include fasteners to facilitate engagement with the spinous processes to provide both a flexion stop as well as an extension stop. The fasteners may have corresponding bores to allow the fasteners to reside in the bores to provide a compact profile for implantation. In another aspect of the invention, the implant is introduced to (Continued)

the surgical site using a lateral or paramedian approach and associated tools to facilitate the same.

20 Claims, 12 Drawing Sheets

(56) References Cited

U.S. PATENT DOCUMENTS

| | | | | |
|---|---|---|---|---|
| 8,109,972 | B2* | 2/2012 | Zucherman | A61B 17/7065 606/249 |
| 8,241,330 | B2 | 8/2012 | Lamborne et al. | |
| 8,795,335 | B1* | 8/2014 | Abdou | A61B 17/7065 606/247 |
| 9,211,147 | B2* | 12/2015 | Gordon | A61B 17/7068 |
| 9,247,968 | B2* | 2/2016 | Taber | A61B 17/7068 |
| 9,364,339 | B2* | 6/2016 | Mayer | A61F 2/442 |
| 9,393,126 | B2* | 7/2016 | Mayer | A61F 2/4425 |
| 2007/0156239 | A1* | 7/2007 | Zipnick | A61B 17/3421 623/17.11 |
| 2007/0239160 | A1* | 10/2007 | Zipnick | A61B 17/320016 606/86 A |
| 2007/0260245 | A1* | 11/2007 | Malandain | A61B 17/025 606/250 |
| 2008/0027438 | A1* | 1/2008 | Abdou | A61B 17/7062 606/249 |
| 2008/0039944 | A1* | 2/2008 | Malandain | A61B 17/7065 623/17.16 |
| 2008/0051893 | A1* | 2/2008 | Malandain | A61B 17/7065 623/17.11 |
| 2008/0058934 | A1* | 3/2008 | Malandain | A61B 17/025 623/17.11 |
| 2008/0091269 | A1* | 4/2008 | Zipnick | A61B 17/320016 623/17.13 |
| 2008/0108990 | A1* | 5/2008 | Mitchell | A61B 17/7068 606/305 |
| 2008/0140125 | A1* | 6/2008 | Mitchell | A61B 17/1606 606/279 |
| 2008/0161818 | A1* | 7/2008 | Kloss | A61B 17/025 606/90 |
| 2008/0167657 | A1* | 7/2008 | Greenhalgh | A61B 17/7065 606/90 |
| 2008/0177391 | A1* | 7/2008 | Mitchell | A61B 17/7065 623/17.16 |
| 2008/0183211 | A1* | 7/2008 | Lamborne | A61B 17/7068 606/249 |
| 2008/0195152 | A1* | 8/2008 | Altarac | A61B 17/7065 606/249 |
| 2008/0281359 | A1* | 11/2008 | Abdou | A61B 17/7068 606/246 |
| 2008/0319549 | A1* | 12/2008 | Greenhalgh | A61B 17/025 623/17.16 |
| 2009/0054988 | A1* | 2/2009 | Hess | A61B 17/025 623/17.16 |
| 2009/0093883 | A1* | 4/2009 | Carrasco | A61B 17/7062 623/17.16 |
| 2009/0138045 | A1* | 5/2009 | Ciupik | A61B 17/7067 606/249 |
| 2009/0138046 | A1* | 5/2009 | Altarac | A61B 17/7065 606/249 |
| 2009/0198241 | A1* | 8/2009 | Phan | A61B 17/7065 606/90 |
| 2009/0198338 | A1* | 8/2009 | Phan | A61B 17/7065 623/17.16 |
| 2009/0222043 | A1* | 9/2009 | Altarac | A61B 17/7065 606/249 |
| 2009/0234389 | A1* | 9/2009 | Chuang | A61B 17/7065 606/249 |
| 2009/0254185 | A1* | 10/2009 | Dollinger | A61B 17/7065 623/17.16 |
| 2009/0292316 | A1* | 11/2009 | Hess | A61B 17/7065 606/249 |
| 2009/0326581 | A1* | 12/2009 | Galley | A61B 17/7065 606/249 |
| 2010/0036419 | A1* | 2/2010 | Patel | A61B 17/7065 606/249 |
| 2010/0087869 | A1* | 4/2010 | Abdou | A61B 17/70 606/279 |
| 2010/0211101 | A1 | 8/2010 | Blackwell et al. | |
| 2011/0022090 | A1* | 1/2011 | Gordon | A61B 17/7068 606/249 |
| 2011/0166600 | A1* | 7/2011 | Lamborne | A61B 17/7068 606/249 |
| 2011/0172711 | A1* | 7/2011 | Kirschman | A61B 17/7058 606/252 |
| 2011/0184468 | A1* | 7/2011 | Metcalf, Jr. | A61B 17/7068 606/279 |
| 2011/0313458 | A1* | 12/2011 | Butler | A61B 17/7065 606/249 |
| 2011/0319936 | A1* | 12/2011 | Gordon | A61B 17/7068 606/248 |
| 2012/0089185 | A1 | 4/2012 | Gabelberger | |
| 2012/0143341 | A1* | 6/2012 | Zipnick | A61B 17/320016 623/17.16 |
| 2012/0191135 | A1* | 7/2012 | Abdou | A61B 17/7068 606/248 |
| 2012/0265204 | A1* | 10/2012 | Schmierer | A61B 17/1671 606/70 |
| 2013/0041408 | A1* | 2/2013 | Dinville | A61B 17/7065 606/249 |
| 2013/0184753 | A1* | 7/2013 | Keiper | A61B 17/7047 606/248 |
| 2013/0226240 | A1* | 8/2013 | Abdou | A61B 17/7067 606/248 |
| 2014/0031869 | A1* | 1/2014 | Carlson | A61F 2/447 606/264 |
| 2014/0343608 | A1* | 11/2014 | Whiton | A61B 17/7068 606/249 |
| 2015/0313650 | A1* | 11/2015 | Taber | A61B 17/7067 606/249 |

OTHER PUBLICATIONS

"European Application Serial No. 13866660.7, Extended European Search Report mailed Nov. 11, 2016", 11 pgs.

* cited by examiner

INTERSPINOUS IMPLANTS WITH ADJUSTABLE HEIGHT SPACER

CROSS-REFERENCE TO RELATED APPLICATIONS

This application is related to U.S. patent application Ser. No. 11/934,604, filed Nov. 2, 2007, now U.S. Pat. No. 8,241,330, titled Spinous Process Implants and Associated Methods; U.S. patent application Ser. No. 12/020,282, filed Jan. 25, 2008, titled Spinal Implants and Methods; U.S. patent application Ser. No. 12/751,856, filed Mar. 31, 2010, titled Spinous Process Implants and Associated Methods; U.S. patent application Ser. No. 12/538,710, filed Aug. 10, 2009, now U.S. Pat. No. 8,382,801, titled Spinous Process Implants, Instruments, and Methods; and U.S. patent application No. 12/854,125, filed Aug. 10, 2010, titled Interspinous Implants and Methods, all of which are incorporated herein by reference as if set out in full.

FIELD

The present disclosure relates to interspinous implants that facilitate distraction and fusion of a spine and, more particularly, to an interspinous implant that may be easier to implant percutaneously.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age or injury, spinal discs begin to break down, or degenerate, resulting in the loss of fluid in the discs, and consequently, the discs become less flexible. Likewise, the discs become thinner allowing the vertebrae to move closer together. Degeneration also may result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

Rather than spinal fusion, investigators have promoted the use of motion preservation implants and techniques in which adjacent vertebrae are permitted to move relative to one another. One such implant that has met with only limited success is the artificial disc implant. The artificial disc typically includes either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed. The extension stop spacers, however, also have had limited success.

Recently, the trend has been back towards fusion devices rather than motion preservation devices. One promising recent implant is a spinal process fusion plate. Similar to the fusion implants, the spinal process fusion plate promotes fusion between adjacent vertebrae to relieve pressure on the nerve. However, unlike more conventional spinal implant systems, the spinal process fusion plate facilitates less invasive procedures than conventional spinal fusion surgery. The need still exists for improved spinal process fusion plates to facilitate even less invasive surgery including, minimally invasive surgery, percutaneous implantation, and the like.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

DESCRIPTION OF THE ILLUSTRATIVE EXAMPLES

Figure 1:
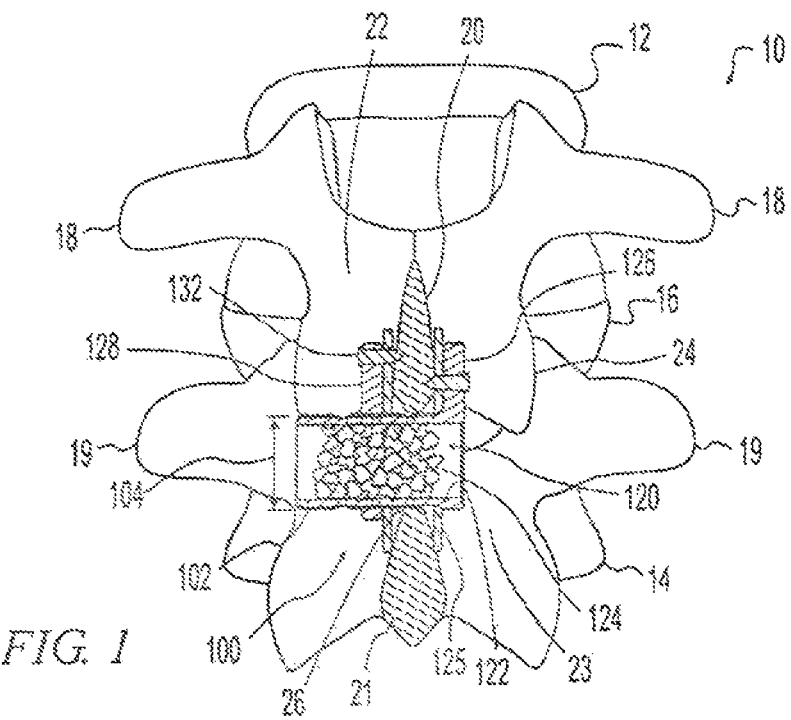
FIG. 1 is a posterior cross sectional view of an implant in situ that is deployed using a tool consistent with the technology of the present application.

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. Further, the instrument(s) described in accordance with the technology of the present application facilitate surgical implantation of spinal process fusion plates. With that in mind, exemplary spinous process implants, according to the technology, may include a spacer and an extension extending outwardly from the spacer. The extension, which may be referred to as a wing, is sometimes described as being one or more lobes associated with the spacer. In certain aspects, the spacer may be integral or monolithic with one of the extensions. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer and extensions may include openings, recesses, pockets, etc. to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer or a hole, pocket, or recess in the extensions. A hollow interior may be configured to receive bone growth promoting substances such as by packing the substances into the hollow interior. The openings may be relatively small and/or comprise pores or interconnecting pores over at least a portion of the spacer surface. The openings, however formed, may be filled with bone growth promoting substances.

Whether unitary or modular, the extension may extend transversely from the spacer relative to a spacer longitudinal axis to maintain the spacer between adjacent spinous processes. The extension may be described as foldable, extendable, deployable or the like from a flat configuration to facilitate minimally invasive implantation to an extended position to facilitate fusion. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is moveable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material.

Insertion of spinous process implants may be facilitated by a set of instruments alternately engageable with one another to increase the interspinous space and engageable with a spinous process implant to help maneuver it between adjacent spinous processes as has been described in some of the related applications described above and incorporated by reference. Moreover, instruments for the present spinous process implant may facilitate percutaneous operation whether through a cannula, tube, or lumen. The instruments may include mechanisms to facilitate unfolding, opening, or deploying foldable extensions. The instruments may include a draw internal or external to the spacer to pull the extensions in a direction such that the extensions are pried apart by a wedge or ramp.

It has been found that presently available interspinous implants, such as the device explained with reference to FIGS. 1-9, are good at stabilizing a spinal segment to allow it to fuse. The interspinous implant could be implanted with less tissue trauma percutaneously or through a tube, cannula, or lumen if the spacer was provided in a compact state and expanded to a distraction state subsequent to the placement of the spacer between adjacent spinous processes. In certain embodiments, the implant, when in the compact state, fits within the space between adjacent spinous processes without abutting both processes. In other embodiments, the implant may slightly distract the spinous processes when in the compact state. Expanding the spacer to the distraction state may be subsequent to manual distraction of the vertebral bodies or may be in conjunction with expanding the spacer. Expanding the spacer may be accomplished by providing a spacer body with a superior and inferior portion that have internal surfaces that are ramped to cooperatively engage an internal body that is wedge shaped or ramped such that drawing the internal body laterally through an interspinous space may cause at least one of the superior and inferior portions to move apart in a distraction direction. In other embodiments, the spacer may be mounted on a post that telescopes into a bore such that the post may be expanded from the bore to cause expansion.

In certain embodiments, one or both of the extensions may be a foldable or collapsible extension to further compact the implant prior to placement. One or more of the extensions may have offset fasteners on the foldable extension and corresponding bores into which the fasteners may fit to allow a flat or nearly flat configuration of the folded wing for the most compact delivery possible. The foldable extensions may fold about an axle or be hinged to allow for movement. A draw, rod, or hook may be connected to the hinge or axle to pull the hinge or axle towards the spacer that causes the face or surface of the extension to run up against an edge that forces the folded extension to unfold. In some embodiments, internal rods and ramps may be used to force the folded extension to unfold or open.

Reference will now be made to FIGS. 1-9 describing an exemplary embodiment of a spinous process implant with a fixed and non-expandable spacer as well as at least one fixed or non-foldable extension. As will be explained further below, the spacer may be replaced with an expandable spacer that is expandable before or after implantation from a compact or insertion state to a distraction or expanded state. For completeness, however, the description of the spinous process implant with a fixed and non-expandable spacer is provided for completeness. While a specific exemplary embodiment is provided herein, implants associated with any of the incorporated applications or similar spinous process fusion plates may benefit from the technology of the present application to allow fixed extensions or wings to fold to facilitate implantation. Moreover, it may be especially beneficial to incorporate a foldable extension with the technology of the present application.

Figure 2:
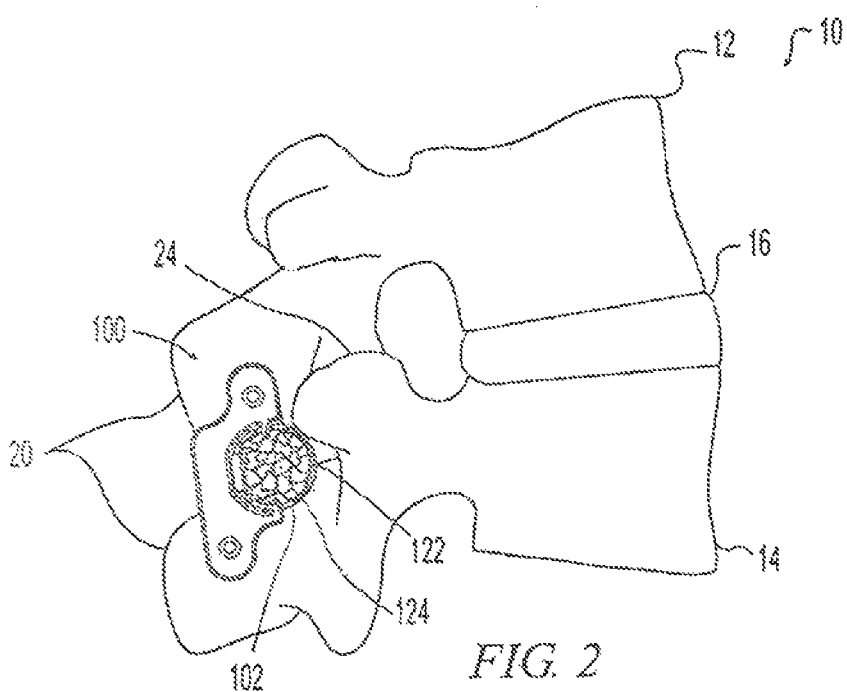
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The geometry of the implant 100 is illustrated with the use of axes that define length (l), height (h), and width (w) directions for the spacer. When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of spacer 102 limits how closely the spinous processes 20, 21 can move together. As the implant in this example is a fusion plate, the height also limits how distantly the spinous processes 20, 21 can move apart. Thus, the spacer 102 maintains a minimum and maximum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
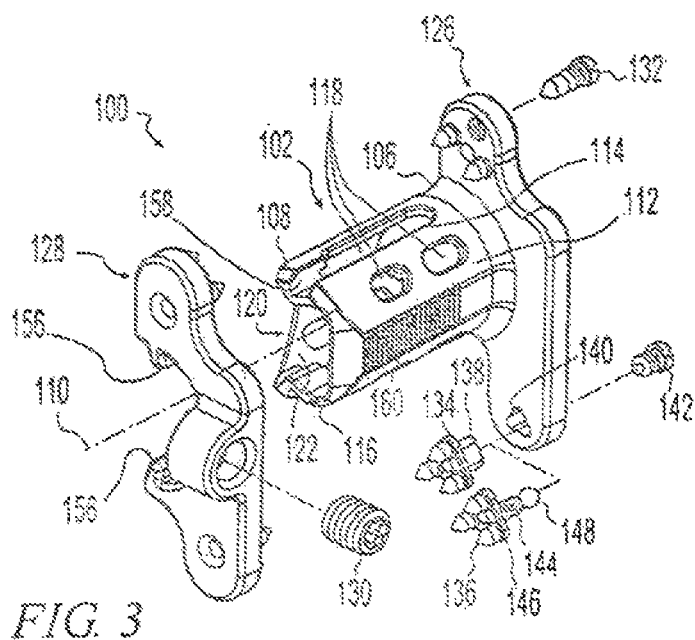
FIG. 3 is an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102. When fixed, the first extension 126 may be generally unitary with spacer 102 or the first extension 126 and spacer 102 may form a monolithic unit. The implant 100 also includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts an additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. As an alternative to strips of bone 125, the bone 125 may be formed similar to a washer or ring to cooperatively fit about the fasteners 132, 134, 136 to promote bone growth. While the extensions 126, 128 may extend in only one of inferiorly or superiorly from the spacer 102, the extensions 126, 128 preferably extend inferiorly as well as superiorly from spacer 102 to optionally attach to both the inferior and superior spinous processes to immobilize the spinous processes 20, 21 relative to one another while fusion takes place.

Fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured, such as by screw 142, to adjust the tension in the joint and/or to lock the fastener 136 in a predetermined orientation.

Figure 4:
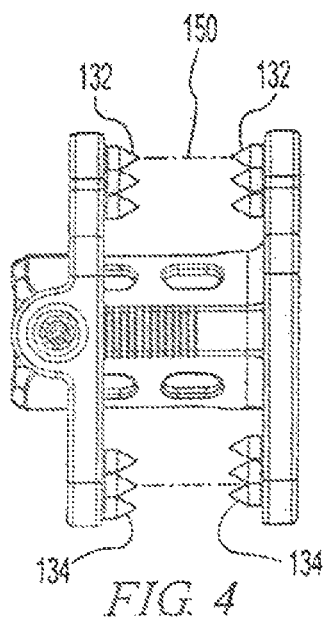
FIG. 4 is a posterior elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave, if necessary, as they are pressed into a bone. Any combination of fastener type, number, and alignment may be provided on the implant 100.

Figure 5:
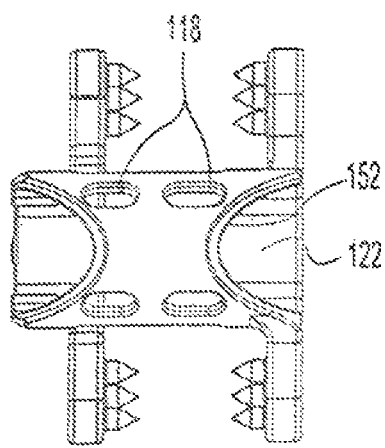
FIG. 5 is an anterior elevational view of the implant of FIG. 1.
Figure 6:
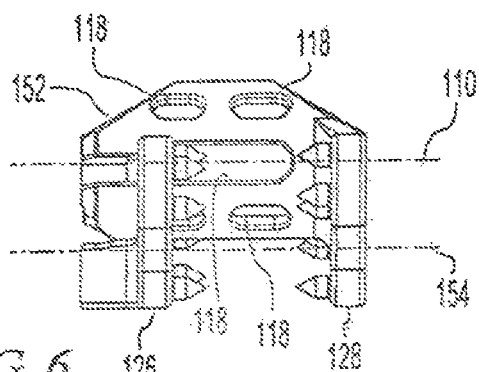
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
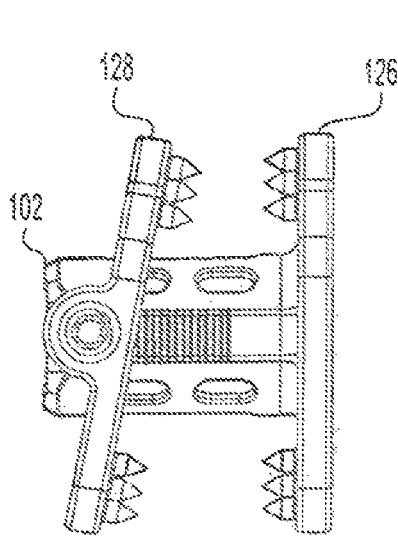
FIG. 7 is a posterior elevational view of the implant of FIG. 1 showing the assembly in an alternate position.
Figure 8:
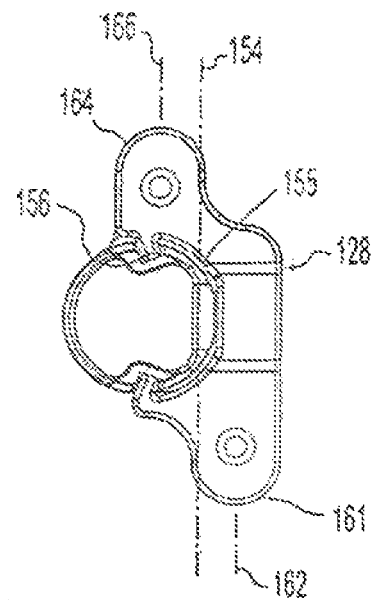
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape, although the aperture 155 could conform to the entire cross-section of the spacer to form a "D" or "O" shape, for example. In the exemplary embodiment, aperture 155 forming a generally "C"-shape includes tabs 156 that extend inwardly from the superior and inferior portions of the aperture to slidingly engage elongated slots 158 in the superior and inferior surfaces of the spacer 102. The second extension 128 can be translated longitudinally along the spacer length l toward and away from the first extension 126. Tightening the set screw 130 against the posterior side 160 of the spacer 102 forces the tabs 156 posteriorly against the sides of the slots 158 and locks the second extension 128 in place longitudinally. The tabs 156 may increase towards the tip of the tabs 156 to facilitate engagement with the slots 158 in the spacer 102. The tabs 156 may be hooked shaped as well instead of straight or expanding to facilitate the cooperative engagement. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
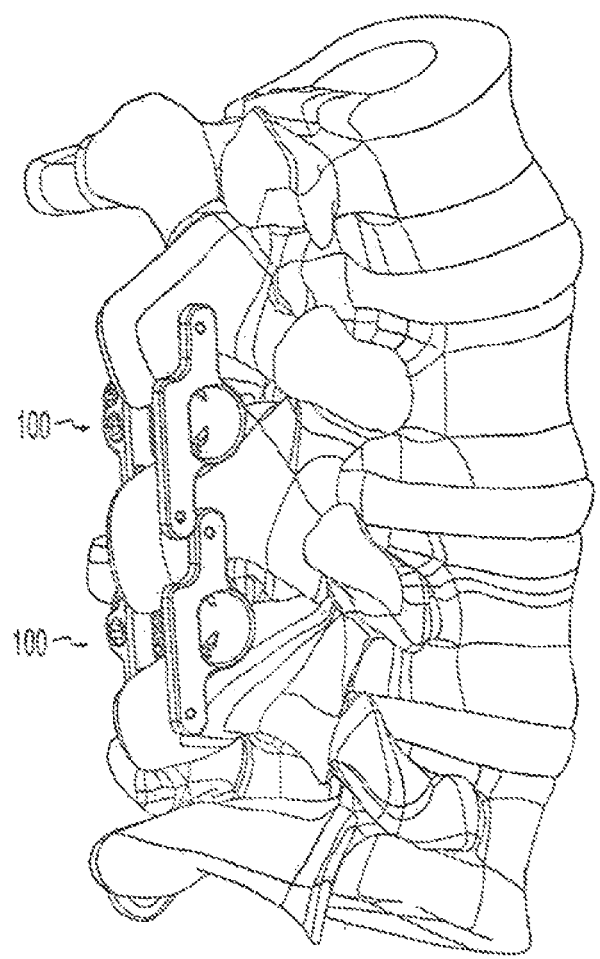
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface radius $r_4$, while second superior lobe radius $r_3$ is substantially equal to inferior concave surface radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition, the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162,166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

As shown in FIGS. 1-9, the first extension 126 is integral or unitary with the spacer 102 and second extension 128 has an aperture 155 that is shown to partially surround the spacer to allow the second extension 128 to translate over the outer surface of the spacer 102. In certain embodiments, especially smaller implants, the aperture 155 may form a through hole in second extension 128 to completely surround the spacer 102.

Figure 10:
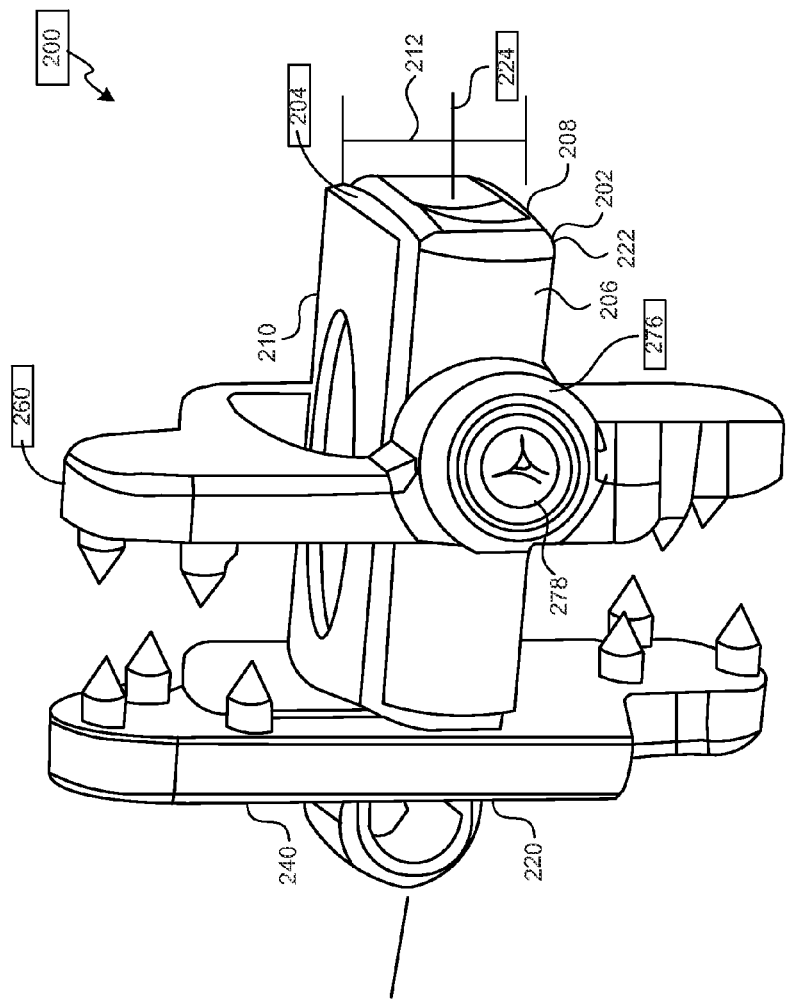
FIG. 10 is a perspective view of an implant that is consistent with the technology of the present application.
Figure 11:
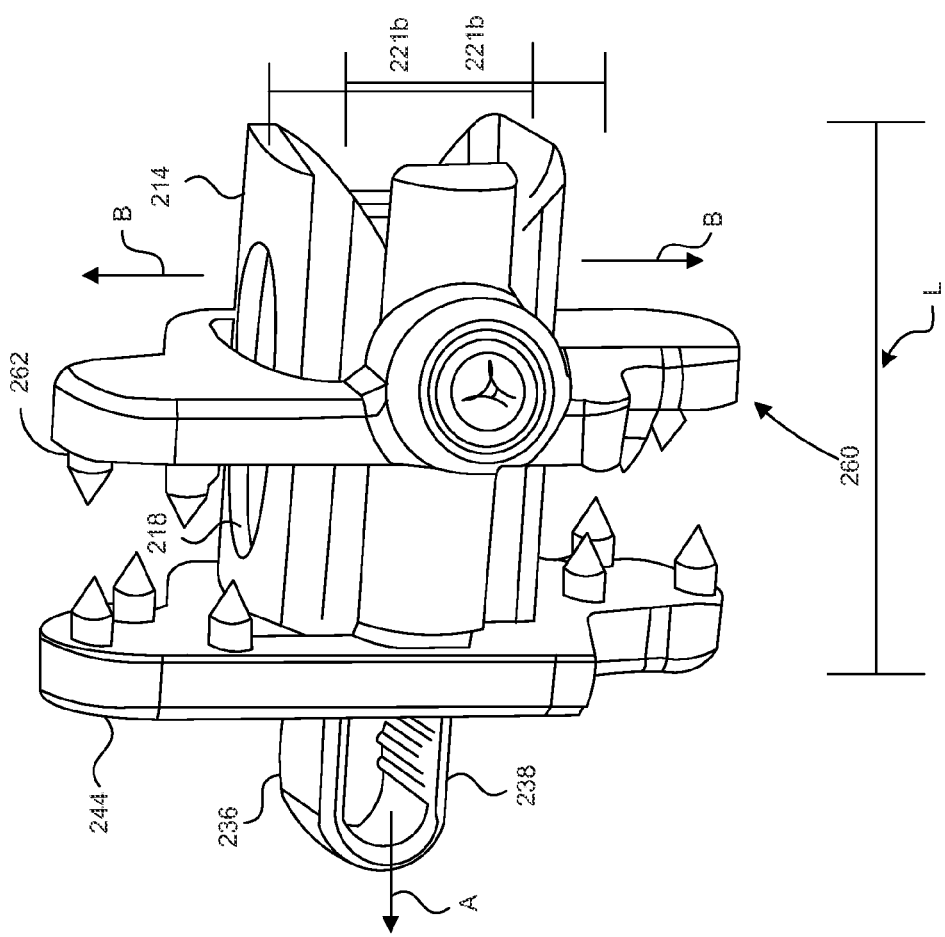
FIG. 11 is another perspective view of the implant of FIG. 10.
Figure 12:
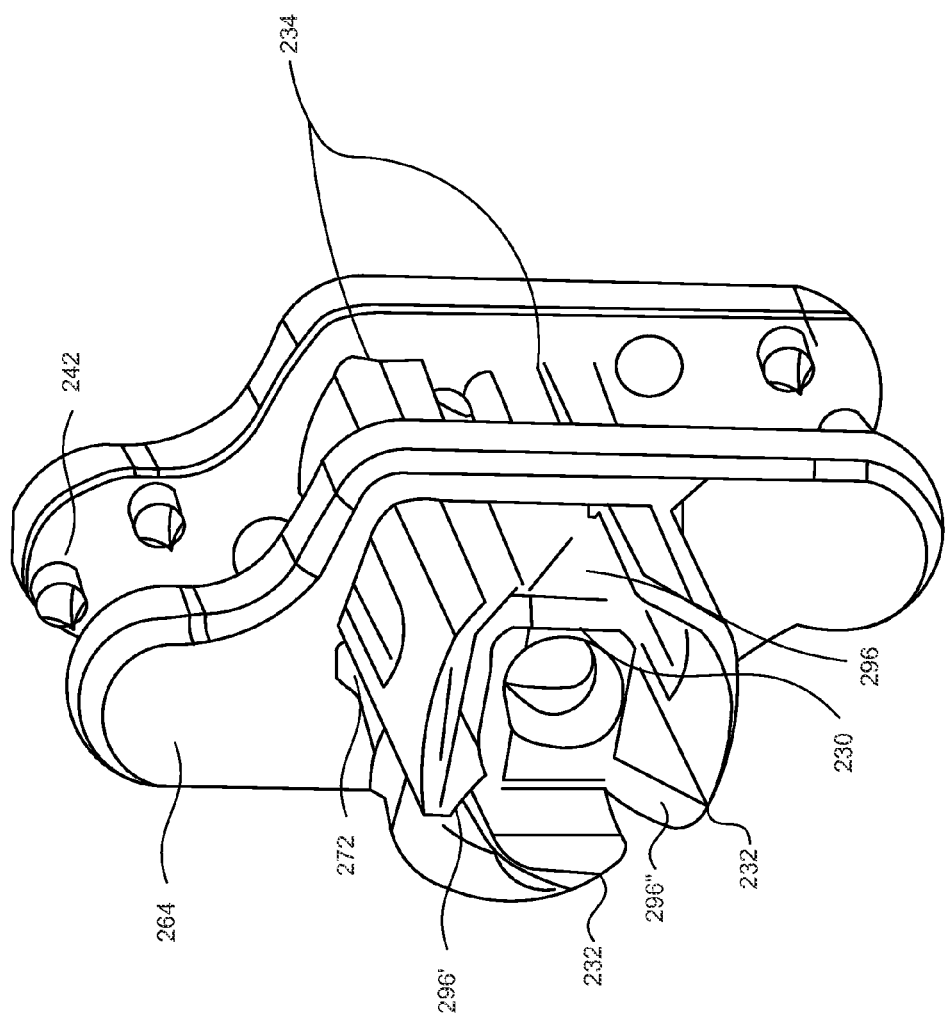
FIG. 12 is another perspective view of the implant of FIG. 10.

FIGS. 10, 11, and 12 provide perspective views of an exemplary implant 200. The implant 200 includes a spacer body 202 comprising a superior wall 204, a posterior wall 206, and an inferior wall 208 as will be explained further below. The exemplary implant 200 is shown without an anterior wall, although one could optionally be provided. FIG. 10 shows the implant 200 with the spacer body 202 in a first configuration 210 where the superior wall 204 and the inferior wall 208 are arranged in a compact state to facilitate insertion of the implant 200. In the first configuration 210, the superior wall 204 and the inferior wall 206 may be separated a first distance 212 in the height direction, which is the cephalic/caudal direction. While not necessary, the first distance 212 may be less than the minimum separation of adjacent spinous processes. Generally, this allows insertion of the spacer body 202 into the interspinous spacer with less resistance as the spacer body 202 may contact only one or, in certain embodiments, neither of the adjacent spinous processes during insertion.

As will be explained further below, the implant 200 may be further fixed to the spinous processes such that the implant 200 also limits how far the spinous processes can move apart such that the implant 200 is a flexion inhibiter as well, which facilitates fusion as the spinal segments are immobilized with respect to each other. Generally, the adjacent spinous processes may be distracted prior to fixing the implant to the spinous processes to facilitate distraction. The distraction, as will be further explained below, may be caused by expanding the spacer body 202 to a second configuration 214, where the spacer body 202 is distracted into a distraction state. In the distraction state of the second configuration 214, the superior wall 204 and the inferior wall 208 may be separated a second distance 216 in the height direction where the second distance is greater than the first distance. The superior wall 204 and the inferior wall 208 would abut the respective spinous processes, such as, spinous processes 20, 21. As will be appreciated on reading the disclosure, providing an implant where the separation between the superior wall 204 and the inferior wall 208 allows for the provision of fewer implants or spacers as each implant provided in a kit covers a variety of distraction ranges. Moreover, as explained above, the insertion of the implants in the collapsed configuration facilitates the ease of insertion of the implant, including the reduced lateral loads on the spinous process during the procedure, which should reduce the possibility of fracture of the bone. The distraction of the spacer provides tactile feedback to the surgeon in the form of resistance to facilitate adjustment of the final separation between the superior and inferior walls 204, 208.

The spacer body 202 has a first end 220, a second end 222, and a longitudinal axis 224 along a length L of the spacer. The spacer body 202 is generally shown as a rectangular or cylindrical shape in the present application, although many other shapes are possible to accommodate patient anatomy. Moreover, the spacer body 202 having superior and inferior walls 204, 208 that may be spaced a select distance apart as explained herein provides for a spacer that may be more adaptable for patient anatomy. The longitudinal axis 224 is approximate the geometric center of the spacer body 202 as shown in the first configuration 210. The length L of the spacer is in the medial/lateral direction. The length L is sufficient to allow the spacer 202 to traverse an interspinous space between adjacent spinous processes, such as processes 20, 21.

The spacer 202 may include opening 218 in the superior and inferior wall 204, 208. Also, the posterior wall 206 may include an opening 218, not shown in the figures. The opening 218 may be elongated slots as shown, bores, perforations, micro pores, or the like. The openings 218 allow for tissue or bony in-growth to form between the adjacent spinous processes to facilitate fusion. The spacer 202 may be filled with bone growth promoting substances as described above.

Figure 15:
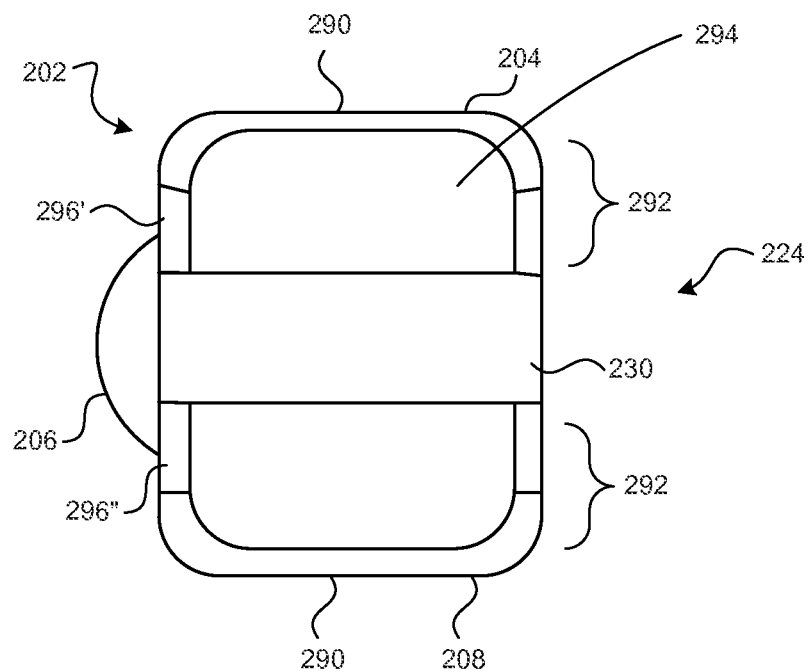
FIG. 15 is a view of a spacer body of the implant of FIG. 10.

As best shown in FIGS. 12 and 15, a block 230 resides between the superior and inferior walls 204, 208. The block 230 may be hollow as shown. The block 230 may be formed from graft material, such as PEEK, to promote bone growth. As will be explained further below, movement of the block 230 along the spacer body 202 between the first and second ends 220, 222 causes the superior and inferior walls 204, 208 to distract or retract between the first and the second configurations 210, 214. For purposes of the technology of the present application, the first configuration is relatively more compact in the height direction than the second configuration. The first configuration may be at its most compact configuration when the block 230 is aligned with the distal edge 232 of the second end 222 and the second configuration may be at its most distracted configuration when the block 230 is aligned with the proximal edge 234 of the first end 220. Fixation of the block 230 between the distal edge 232 and the proximal edge 234 allows the surgeon to select a distraction height between the height 212 and height 216.

The block 230 includes a draw 236, which in this exemplary embodiment is a loop of material coupled to one end of the block 230. The loop provides a natural pull/push point for moving the block 230, but the loop could be replaced by a straight piece of material, such as a beam or rod, a hook of material, or the like to allow a tool to grasp and pull/push the draw. The draw 236 is used to move the block as will be explained further below. The draw 236 may have protrusions 238. The protrusions 238 could be used to form a ratchet and pawl type of locking device to secure the placement of the block 230 or, in certain embodiments, the protrusions 238 could be used as teeth that mate with an associated gear (not specifically shown) to drive the draw 236 on rotation of the gear similar to a rack and pinion gearing system as is generally known in the art. Moving the draw 236 in the direction of arrow A will cause the block 230 to move towards the first end 220, which causes the relative movement of the superior and inferior walls 204, 208 in the direction of arrows B.

Figure 13:
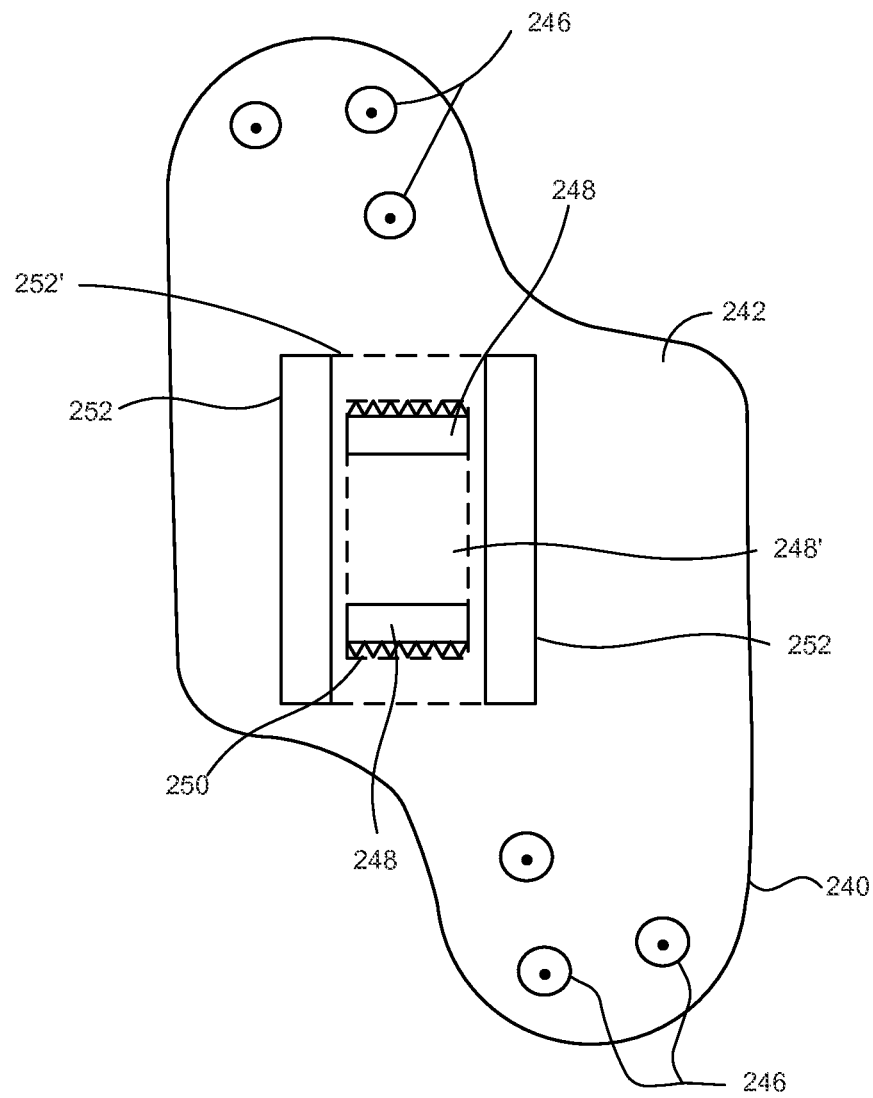
FIG. 13 is a view of an extension of the implant of FIG. 10.

Implant 200 includes a first extension 240 having a medial facing surface 242 and a lateral facing surface 244. The posterior wall 206, in this exemplary embodiment, cantilevers from the medial facing surface 242 of the first extension 240 and is adapted to traverse the interspinous space. The first extension 240 may be called a post plate as the posterior wall 206 may be integral with the first extension 240 such that the plate has an affixed post. FIG. 13 shows a view of the medial facing surface 242 of the first extension 240 with the spacer body 202 removed for clarity. The medial facing surface 242 has a series of fasteners 246 extending in the length direction to facilitate engaging with the spinous processes. The medial facing surface 242 may have a pair of bores 248 arranged to cooperatively engage the draw 236. In particular, the draw 236, as shown, is a loop with two legs that extend through the bores 248 to connect to the block 230. The bores 248 allow the draw 236 to move in the length direction with respect to the first extension 240. Moreover, the bores may have surface striations 250 to engage the protrusions 238 in a ratchet and pawl lock or the like. Alternatively, instead of a pair of bores 248, there may be a single bore 248' to allow the draw to move. The bores 248 are sized such that the block 230 cannot be pulled completely through the first extension 240. The medial facing surface 242 also includes a pair of channels 252 extending in the height direction. The channels 252 may be through holes or not. The channels 252 are sized to cooperatively receive protrusions extending from the superior and inferior walls 204, 208 at the first end 220 of the spacer body 202, as will be explained further below. The channels 252 may be undercut to accept flared, dovetailed, or flanged surfaces on the superior and inferior walls 204, 208 to facilitate retention of the superior and inferior walls 204, 208 in a sliding relationship with the first extension 240. The edge of the first end of the superior and inferior walls 204, 208 would be configured to slide along the medial facing surface 242. The pair of channels 252 could be a single channel on either the anterior or posterior side of the first extension 240. Also, the channel or channels could be divided into superior and inferior channels as well associated individually with the superior or inferior walls 204, 208. Rather than protrusions extending from the edge of the superior and inferior walls 204, 208 as shown by the exemplary embodiment herein, the medial facing surface 242 may have a recess 252', as shown in phantom, that fits the ends of the superior and inferior walls 204, 208.

Figure 14:
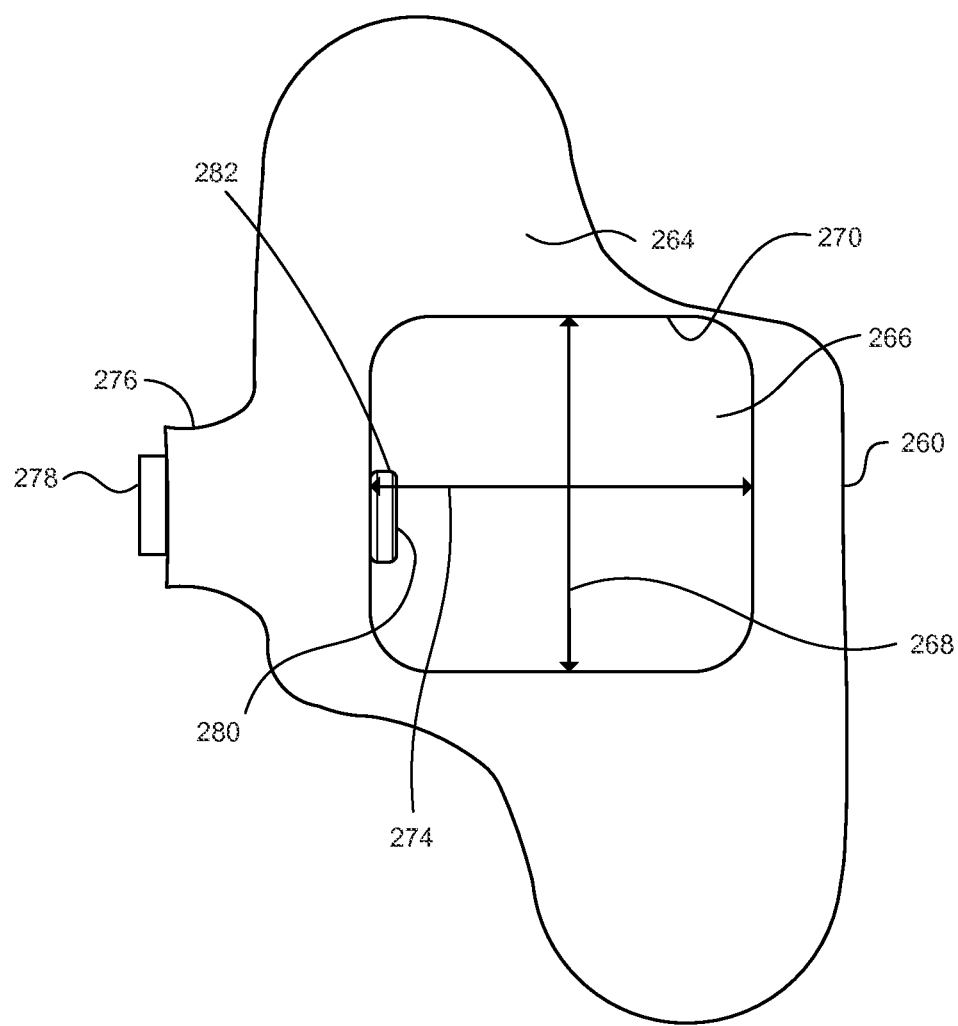
FIG. 14 is a view of an extension of the implant of FIG. 10.

Implant 200 also includes a second extension 260 having a medial facing surface 262 (opposed to medial facing surface 242) and a lateral facing surface 264. The second extension 260, as will be explained below, moves laterally with respect to the spacer body 202 and must be locked in position. Thus, second extension 260 is sometimes referred to as a lock plate. FIG. 14 shows a view of the lateral facing surface 264 of the second extension 260 with the spacer body 202 removed for clarity. The second extension 260 has an aperture 266 sized such that the spacer body 202 fits within the aperture 266 in both the first configuration 210 and the second configuration 214. The aperture 266 has a dimension 268 in the height direction that is larger than the second distance 216. The dimension 268 of aperture 266 may be configured such that the superior and inferior walls 204, 208 abut the inner surface 270 of the aperture 266 when the spacer body 202 is most distracted. Alternatively, the dimension 268 of the aperture 266 may be slightly larger such that a gap 272 exists between the inner surface 270 and the superior and inferior walls 204, 208 to allow for tissue growth. The width 274 of the aperture 266 is sufficient to encompass the spacer body 202 and allow the second extension 260 to translate over the spacer body 202. The aperture 266 may be sized to allow the second extension 260 to be compatible with differently sized spacer bodies 202.

The second extension 260, as mentioned above, translates over the spacer body 202 by allowing relative lateral movement of the spacer body 202 through the aperture 266. When positioned, the second extension 260 is locked to inhibit further relative lateral movement between the spacer body 202 and the aperture 266. In this exemplary embodiment, the second extension 260 has a lock bore 276 into which a lock fastener 278 is fitted in a locking relationship. For example, the lock bore 276 may have internal threads (not specifically shown) that cooperatively engage external threads 280 on a shaft 282 of the lock fastener 278. The tip of the shaft 282 would engage the posterior wall 206 to lock the spacer body 202 with respect to the second extension 260 by, for example, clamping the spacer body 202 to the anterior side of the inner surface 270. Similar to first extension 240, second extension 260 may include fasteners on the medial facing side.

Figure 16:
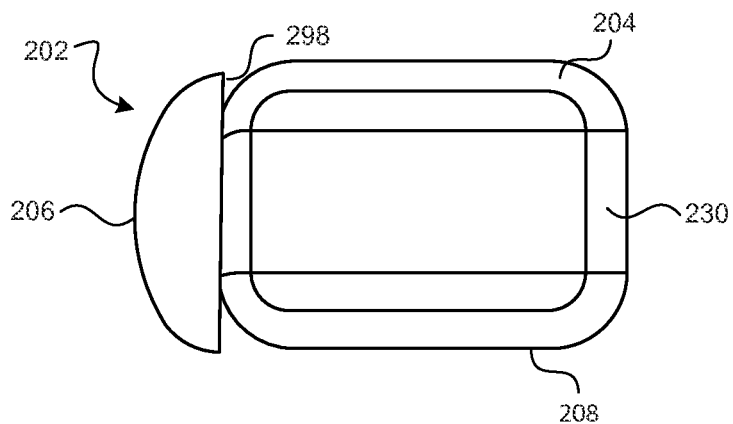
FIG. 16 is a view of a spacer body of the implant of FIG. 10.

Referring now to FIGS. 15 and 16, a lateral view of the spacer body 202 taken from the second end 224 is shown without the first or second extensions 240, 260 for clarity. The spacer body 202 in FIG. 15 is shown in the second configuration 214. The spacer body 202 in FIG. 16 is shown in the first configuration 210. The spacer body 202 includes the superior wall 204, the inferior wall 208, the posterior wall 206, and the block 230 in this exemplary embodiment. An anterior wall may be provided. The superior wall and inferior wall are inverted images of each other and have a first surface 290 adapted to abut the adjacent spinous process as well as a pair of depending walls 292 that extend from the first surface 290 toward the other of the superior or inferior wall 204, 208. A transition from the first surface 290 to the depending walls 292 may be a sharp edge or a beveled edge to reduce tissue trauma as shown. The first surface 290 and depending walls 292 form a trough 294 through which block 230 moves.

As can be seen best in FIG. 12, the block 230, superior wall 204, and inferior wall 208 have a series of cooperative ramps 296, 296', 296''. The posterior depending walls 292 of both the superior and inferior wall 204, 208 travel along and are contained by an anterior surface 298 of the posterior wall 206. As can be seen in FIG. 15, in the exemplary embodiment, the depending walls 292 are contained and aligned by the anterior surface 298 of the posterior wall 206. The anterior surface 298 provides a guide to allow spacer body 202 to be distracted prior to arranging the second extension 260 about the spacer body 202. If the second extension 260 is arranged prior to distracting the spacer body 202, the anterior depending walls 264 of both the superior and inferior walls 204, 208 travel along and are contained by the inner surface 270 of aperture 266.

Figure 17:
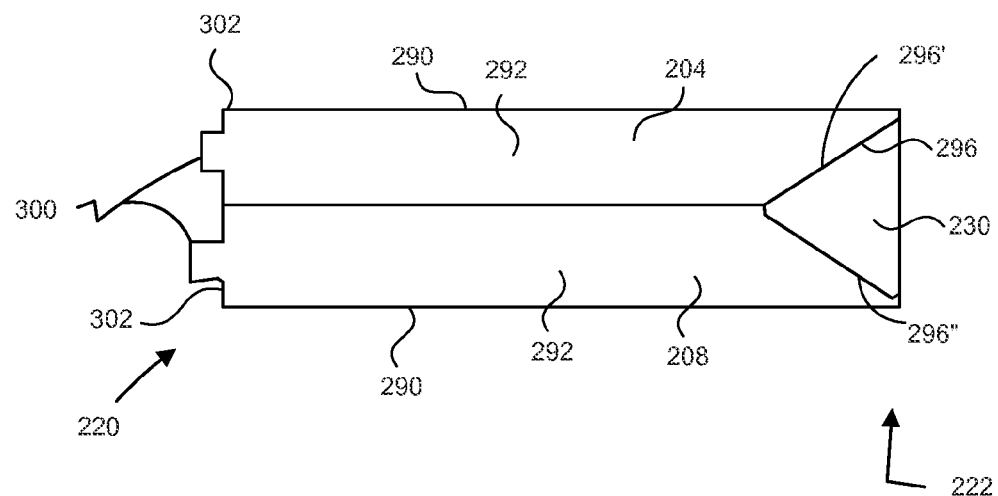
FIG. 17 is a view of a spacer body of the implant of FIG. 10.

Referring now to FIG. 17, a view of the spacer body 202 taken from the anterior aspect is provided without the first or second extension 240, 260 for clarity. The spacer body 202 is shown in the first configuration 210 in FIG. 18. Superior and inferior walls 204, 208 are shown symmetrical in this exemplary embodiment, however, they may be asymmetrical. As shown, superior and inferior walls 204, 208 have protrusions 300 extending from the first end 220 of the spacer body 202. The protrusions 300 are shaped to cooperatively engage the channels 252. The protrusions 300 may be flared to form a dovetail with the channels 252 or have shoulders/flanges to engage an undercut in channels 252 to inhibit the spacer body 202 from moving laterally. The superior and inferior walls have proximal edges 302 that allow for movement of the edges against the first extension 240.

Figure 18:
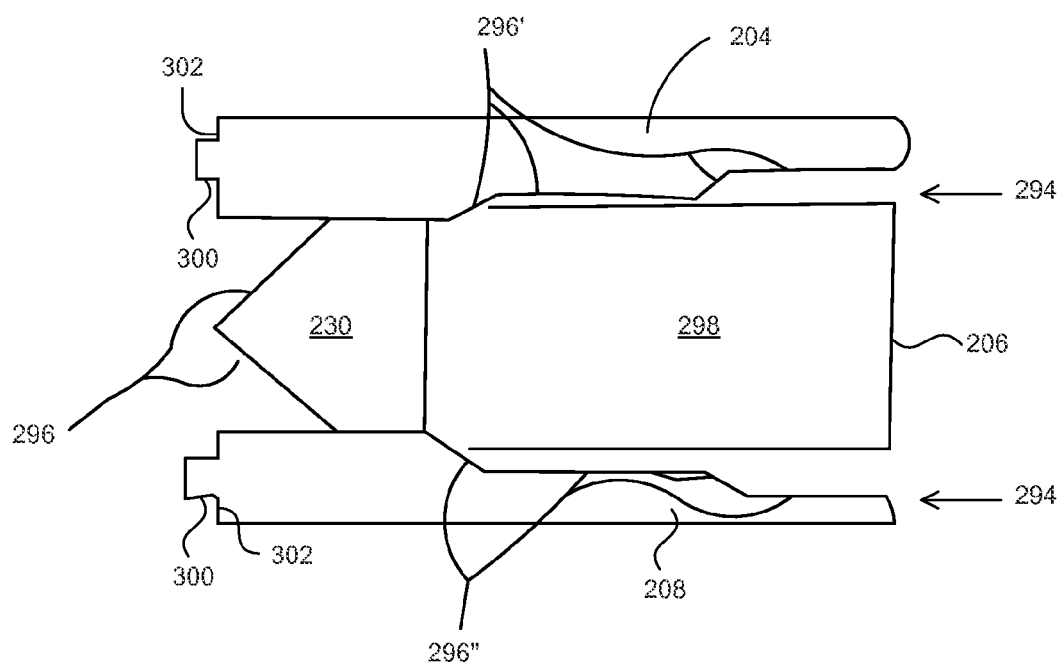
FIG. 18 is a view of a spacer body of the implant of FIG. 10.
Figure 19:
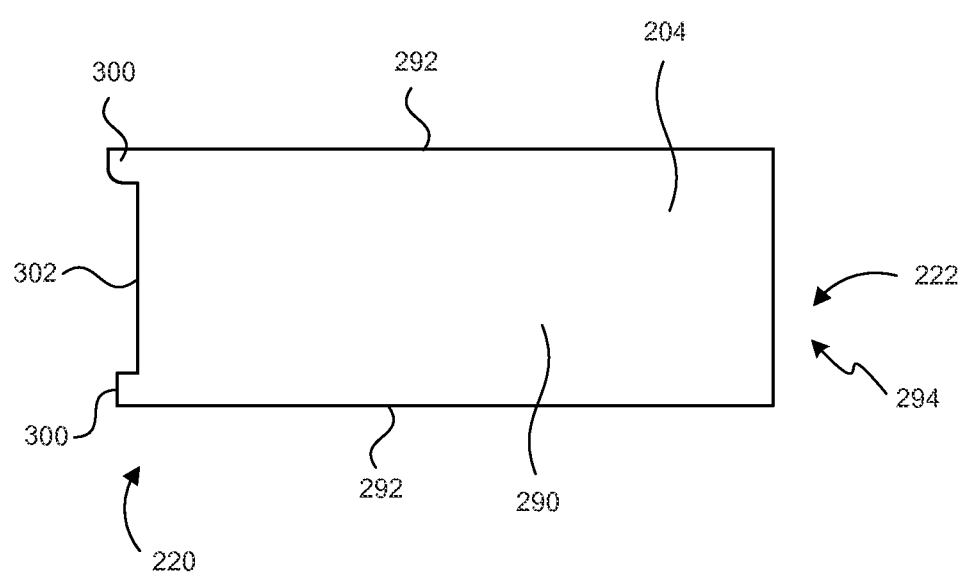
FIG. 19 is a view of a spacer body of the implant of FIG. 10.

The block 230 has ramps 296 that cooperatively engage the ramps 296' and 296" on the superior and inferior walls 204, 208. The ramps are shown as a constant slope; however, the ramps may have cooperative compound slopes instead of a constant slope. The ramps may also be concave or convex curved surfaces. FIG. 18, which shows the spacer body 202 in the second configuration 214, has an alternative construction of the ramps 296' and 296" providing a stepped surface. As can be appreciated, the anterior surface 298 of the posterior wall 206 is visible from the anterior view when the spacer body 202 is in the second configuration. For completeness, FIG. 19 shows a view of the spacer body 202 taken from the superior aspect provided without the first or second extension 240, 260 for clarity.

A number of surgical techniques are possible to insert the implant 200 to the surgical site, such as, for example, a posterior approach that may or may not sacrifice the superspinous ligament, a paramedian approach, a lateral approach, open, percutaneous, a lumen or cannula, or the like. Once the implant is located, the spacer body 202 with the first extension is moved such that the spacer body traverses the interspinous space between adjacent spinous processes. The spacer body 202 would be in the first configuration 210 such that the spacer body 202 has minimal or no contact with the adjacent spinous processes as it traverses the space. The spacer body 202 would generally be moved until the first extension 240 is adjacent to the superior and inferior spinous processes. The second extension 260 is generally arranged over the spacer body 202 prior to distraction of the spacer body 202 from the first configuration 210 to the second configuration 214; however, the second extension 260 optionally may be arranged over the spacer body subsequent to distraction of the spacer body 202. The spacer body 202 is next distracted by moving the draw 236 laterally in the direction A shown in FIG. 11. Moving the draw 236 correspondingly causes the block 230 to move forcing the cooperatively engaging ramps to cause the superior and inferior walls 204, 208 to move in the direction B shown in FIG. 11 to the second configuration 214. The adjacent spinous processes may be manually distracted before or during the distraction of the spacer body 202. In some uses, the spacer body 202 may be used to facilitate the distraction. In certain embodiments, the tool used such that the spacer body 202 facilitates the distraction may be provided with a load measuring instrument or sensor to allow the surgeon to know or monitory the distraction force used when expanding or distracting the space. Next, the first and second extensions 240, 260 are compressed such that the fasteners 246 engage or mesh with the spinous processes. The second extension 260 is locked by engaging the lock fastener 278.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

We claim:

1. An implant adapted to traverse an interspinous space and promote fusion of the adjacent spinous processes comprising:
    a spacer body comprising a proximal end and a distal end, the spacer body comprising at least a superior wall and an inferior wall, the inferior wall separated from the superior wall by an internal space, the superior wall comprising a superior proximal edge and at least one superior protrusion extending from the proximal end of the superior wall, the inferior wall comprising an inferior proximal edge and at least one inferior protrusion extending from the proximal end of the superior wall, the spacer body comprising a block movable in the internal space from relatively more proximate the distal end to relatively more proximate the proximal end causing the superior wall to move relative to the inferior wall such that the spacer body changes from a first configuration where the superior wall and the inferior wall are separated by a first distance to a second configuration where the superior wall and the inferior wall are separated by a second distance greater than the first distance;
    a first extension comprising a medial facing surface adapted to reside adjacent a spinous process and a lateral facing surface, the medial facing surface cooperatively engaging the at least one superior and the at least one inferior protrusion of the spacer body such that at least one of the superior proximal edge or the inferior proximal edge move along the medial facing surface, the medial facing surface comprising a plurality of fasteners extending medially and adapted to engage the adjacent spinous process; and a draw movable laterally and cooperatively engaged to the block to move the block between the distal end and the proximal end of the spacer body, wherein movement of the draw in a first direction causes the spacer body to distract from the first configuration to the second configuration and movement of the draw in a second direction causes the spacer body to compress from the second configuration to the first configuration.

2. The implant of claim 1 comprising a second extension having a second medial facing surface adapted to reside adjacent a spinous process opposite the first extension and a second lateral facing surface, the second extension comprising an aperture extending from the second lateral facing surface to the second medial facing surface and defined by an inner surface that substantially surrounds the spacer body, the aperture defining a height equal to a third distance that is greater than or equal to the second distance, the second medial facing surface comprising a plurality of fasteners extending medially and adapted to engage the adjacent spinous process, the second extension comprising a locking mechanism to lock the second extension to the spacer body.

3. The implant of claim 1 wherein the first extension comprises at least one through hole and the draw extends through the at least one through hole.

4. The implant of claim 2 wherein the spacer body further comprises a posterior wall having an anterior facing surface fixedly extending from the first extension toward the distal end of the spacer body, the posterior wall sized to extend through the aperture and be cooperatively engaged by the locking mechanism.

5. The implant of claim 4 wherein each of the superior and inferior walls comprise a first surface adapted to abut the adjacent spinous process and a depending sidewall extending from the first surface toward the other of the superior and inferior walls.

6. The implant of claim 5 wherein at least one depending sidewall has a first ramp and the block has a second ramp that cooperatively engages the first ramp to cause the superior and inferior walls to move relative to each other.

7. The implant of claim 6 wherein at least one of the ramps comprises a plurality of ramps.

8. The implant of claim 2 wherein the locking mechanism comprises a bore from a posterior edge of the second extension to the aperture and a fastener comprising a shaft that extends into the aperture to engage the posterior wall.

9. The implant of claim 5 wherein the posterior wall comprises an anterior facing surface against which the depending sidewall moves as the spacer body moves between the first configuration and the second configuration.

10. The implant of claim 1 wherein the draw comprises a plurality of protrusions and forms a rack and pinion gear system with the block.

11. The implant of claim 1 wherein the medial facing surface cooperatively engages the protrusions by providing at least one channel in the medial facing surface in which the protrusions move.

12. The implant of claim 11 wherein the channel is undercut and the protrusions are flanged.

13. A spinous process implant adapted to promote fusion between adjacent spinous processes comprising:
a spacer body comprising a proximal end and a distal end, the spacer body comprising at least a superior wall and an inferior wall, the superior wall comprising a first surface adapted to abut a superior spinous process and a pair of laterally depending sidewalls extending from the first surface inferiorly toward the inferior wall, the inferior wall comprising a second surface adapted to abut an inferior spinous process and a pair of laterally depending sidewalls extending from the second surface superiorly toward the superior wall, at least one of the pair of laterally depending sidewalls having at least a first ramp, the spacer body comprising a block movable between the superior and inferior walls, the block comprising at least a second ramp to cooperatively engage the first, wherein movement of the block causes relative movement of the superior wall and the inferior wall so the spacer body moves from a first configuration where the superior wall and the inferior wall are separated by a first distance to a second configuration where the superior wall and the inferior wall are separated by a second distance greater than the first distance;
a first extension comprising a medial facing surface adapted to reside adjacent a spinous process and a lateral facing surface, the medial facing surface comprising a recess shaped to cooperatively engage the proximal ends of the superior wall and the inferior wall and sized to allow movement of the superior wall and inferior wall between the first configuration and the second configuration; and
a draw cooperatively engaged to the block to move the block between the distal end and the proximal end of the spacer body, wherein movement of the draw in a first direction causes the spacer body to distract from the first configuration to the second configuration.

14. The spinous process implant of claim 13 wherein the first extension comprises a bore in the recess through which the draw extends.

15. The spinous process implant of claim 14 wherein the draw comprises a threaded shaft extending through the bore to cooperatively engage a threaded bore in the block.

16. The spinous process implant of claim 13 further comprising a second extension having a medially facing surface and a laterally facing surface with an aperture extending from the medial facing surface to the lateral facing surface, the aperture sized to allow the spacer body to expand to the second configuration, the second extension comprising a locking mechanism to lock the second extension to the spacer body.

17. The spinous process implant of claim 16 wherein the spacer body comprises a posterior wall integral with and extending from the medially facing surface of the first extension and the locking mechanism comprises a lock bore and a lock fastener wherein the lock fastener extends through the lock bore and impinges on the posterior wall to lock the second extension relative to the spacer body.

18. A method of treating spine disease comprising:
providing an implant comprising a spacer body with a superior wall and an inferior wall separated by an internal space, a block sized to move within the internal space and cooperatively engage the superior wall and inferior wall to cause the superior wall and the inferior wall to move from a first configuration where the superior wall and the inferior wall are separated by a first distance to a second configuration where the superior wall and the inferior wall are separated by a second distance greater than the first distance, the superior wall comprising a superior proximal edge and at least one superior protrusion extending from the proximal end of the superior wall, the inferior wall comprising an inferior proximal edge and at least one inferior protrusion extending from the proximal end of the superior wall, a first extension comprising a medial facing surface having at least one channel to cooperatively engage the at least one superior protrusion and the at least one inferior protrusion, the medial facing surface comprising at least one fastener to engage the spinous process, and a draw cooperatively engaged to the block to move the block between the distal end and the proximal end of the spacer body, wherein movement of the draw in a first direction causes the spacer body to distract from the first configuration to the second configuration and movement of the draw in a second direction causes the spacer body to compress from the second configuration to the first configuration;
inserting the spacer in the first configuration between spinous processes of adjacent vertebrae to provide both an extension stop and a flexion stop until the medial facing surface is proximate the spinous process;
moving the draw and the block of the spacer body causing the superior wall and the inferior wall to distract from the first configuration to the second configuration;
positioning a second extension having at least one fastener adapted to engage the spinous process at least partially over the spacer body until the second extension is proximate the spinous process;
clamping the first extension and the second extension wherein the fasteners engage the spinous processes; and
locking the second extension at a desired location along the spacer relative to the first extension.

19. The method of claim 18 further comprising distracting the spinous processes prior to inserting the spacer.

20. The method of claim 18 wherein the step of moving the draw distracts the spinous processes.

* * * * *

UNITED STATES PATENT AND TRADEMARK OFFICE
CERTIFICATE OF CORRECTION

PATENT NO. : 9,561,060 B2
APPLICATION NO. : 14/650418
DATED : February 7, 2017
INVENTOR(S) : Taber et al.

Page 1 of 1

It is certified that error appears in the above-identified patent and that said Letters Patent is hereby corrected as shown below:

In the Claims

In Column 14, Line 26, in Claim 1, after "and", insert --¶--

Signed and Sealed this
Tenth Day of April, 2018

Andrei Iancu
*Director of the United States Patent and Trademark Office*